(12) United States Patent
Farber

(10) Patent No.: US 12,377,158 B1
(45) Date of Patent: Aug. 5, 2025

(54) ENHANCED PEPTIDE CONSTRUCTS FOR ALBUMIN BINDING

(71) Applicant: Michael Farber, Livingston, NJ (US)

(72) Inventor: Michael Farber, Livingston, NJ (US)

( * ) Notice: Subject to any disclaimer, the term of this patent is extended or adjusted under 35 U.S.C. 154(b) by 0 days.

(21) Appl. No.: 19/010,257

(22) Filed: Jan. 6, 2025

Related U.S. Application Data

(63) Continuation-in-part of application No. 18/764,499, filed on Jul. 5, 2024, now abandoned.

(51) Int. Cl.
*A61K 47/64* (2017.01)
*C07K 14/765* (2006.01)

(52) U.S. Cl.
CPC .......... *A61K 47/643* (2017.08); *C07K 14/765* (2013.01)

(58) Field of Classification Search
None
See application file for complete search history.

(56) References Cited

U.S. PATENT DOCUMENTS

| | | | |
|---|---|---|---|
| 6,218,513 B1 * | 4/2001 | Anthony-Cahill | C07K 14/4746 424/193.1 |
| 7,608,681 B2 * | 10/2009 | Dennis | C07K 16/24 530/300 |
| 2006/0228364 A1 | 10/2006 | Dennis | |
| 2017/0233446 A1 | 8/2017 | Glass | |
| 2019/0169593 A1 * | 6/2019 | Tarsio | A23L 33/17 |

OTHER PUBLICATIONS

Rudikoff et al., Proc Natl Acad Sci USA 79: 1979 (Year: 1982).*
Piche-Nicholas et al., MABS 10(1): 81-94 (Year: 2018).*
Burgess et al., Journal of Cell Biology 111: 2129-2138 (Year: 1990).*
Nilsen et al., Commun Biology 3(181): 1-20 (Year: 2020).*
Moore et al., mAbs 2(2): 181-189 (Year: 2010).*
Dennis MS, Zhang M, Meng YG, Kadkhodayan M, Kirchhofer D, Combs D, Damico LA. Albumin binding as a general strategy for improving the pharmacokinetics of proteins. J Biol Chem. Sep. 20, 2002;277(38):35035-43. doi: 10.1074/jbc.M205854200. Epub Jul. 15, 2002. PMID: 12119302 [Date accessed: Jun. 18, 2024].
Zorzi A, Middendorp SJ, Wilbs J, Deyle K, Heinis C. Acylated heptapeptide binds albumin with high affinity and application as tag furnishes long-acting peptides. Nat Commun. Jul. 17, 2017;8:16092. doi: 10.1038/ncomms16092. PMID: 28714475; PMCID: PMC5520048 [Date accessed: Jun. 18, 2024].
Angelini A, Morales-Sanfrutos J, Diderich P, Chen S, Heinis C. Bicyclization and tethering to albumin yields long-acting peptide antagonists. J Med Chem. Nov. 26, 2012;55(22):10187-97. doi: 10.1021/jm301276e. Epub Nov. 5, 2012. PMID: 23088498. [Date accessed: Jun. 18, 2024].
Michot, N. et al. Albumin binding Nanofitins, a new scaffold to extend half-life of biologics—a case study with exenatide peptide. Peptides vol. 152 (Jun. 2022) 170760. doi: 10.1016/j.peptides.2022. 170760 [Date accessed: Jun. 6, 2024].
KMD Bioscience Co. Ltd., Assay Report [Date accessed, Jul. 8, 2024].

* cited by examiner

*Primary Examiner* — Phuong Huynh
(74) *Attorney, Agent, or Firm* — Michael J. Feigin, Esq.; Feigin and Fridman LLC

(57) ABSTRACT

An albumin binding constructs that enhances the pharmacokinetic performance of therapeutic peptides and proteins, extending their half-lives and reducing administration frequency, is disclosed. The core peptide DICLPRWGCLW (SEQ ID NO: 1) is covalently linked to hydrophilic, flexible glycine-serine (Gly-Ser) linkers of the formula (ggs)xgg where X is 3 to 8 units. These linkers provide strong albumin binding (dissociation constant <20 nanomolar). Some constructs feature the GGSGGSGGSGGRLIEDICL-PRGCLWEDD (SEQ ID NO: 4) peptide and allow fusion of active proteins like Klotho, maintaining biological activity and leveraging albumin's extended half-life. Constructs are produced using cellular expression systems (CHO, HEK293, Transgenic Insect Cells) for scalability. These constructs show prolonged half-lives comparable to at least 90% of native albumin. Klotho constructs using the albumin binder demonstrate FGF23 binding dissociation coefficients between 15-30 nanomolar essentially the same as natural Klotho Designed to minimize antigenicity, these constructs improve drug delivery efficacy and patient outcomes.

5 Claims, No Drawings

Specification includes a Sequence Listing.

ENHANCED PEPTIDE CONSTRUCTS FOR ALBUMIN BINDING

REFERENCE TO SEQUENCE LISTING SUBMITTED ELECTRONICALLY

The contents of the electronic sequence listing (FBR008.2-SequenceListing.xml; Size: 5,453 bytes; and Date of Creation: Oct. 10, 2024) are herein incorporated by reference in their entirety.

FIELD OF THE DISCLOSED TECHNOLOGY

The disclosed technology relates to pharmacological and pharmaceutical drug delivery and proliferation. More specifically, the disclosed technology relates to a peptide construct that binds active proteins to circulating albumin in a subject.

BACKGROUND OF THE DISCLOSED TECHNOLOGY

Pharmaceutical research has focused on enhancing the pharmacokinetics of therapeutic peptides and proteins in humans and mammals by binding them to albumin. Various methods like short peptide constructs, modified peptides, acylated peptides, Xtend additions, fusion to IgG or partial IgG moieties, PEGylation, and Nanofitin constructs have been employed for this purpose.

Albumin, a key protein in plasma with a molecular mass of about 67 kDa and a half-life of 19 days in humans, plays a critical role in drug delivery. Previously peptide phage display technology has identified peptides containing the core sequence DICLPRWGCLW (SEQ ID NO: 1) that bind albumin with high affinity at sites distinct from small molecule binding sites. For instance, the natural amino acid sequence (Ac-RLIEDICLPRWGCLWEDD-NH2) (SEQ ID NO: 2) binds albumin with dissociation constants of 266±8 nM (rat), 320±22 nM (rabbit), and 467±47 nM (human), significantly extending half-lives when administered intravenously in rabbits.

Fusions of albumin-binding peptides such as those referred to above when covalently joined with therapeutic proteins, such as the anti-tissue factor Fab of D3H44, have shown enhanced pharmacokinetics with prolonged half-lives in animal models, surpassing traditional strategies. These advancements, coupled with protein fusions, glycosylation, and PEGylation techniques, demonstrate the potential to optimize drug exposure by leveraging albumin's natural carrier function.

U.S. Pub. 2006/0228364 to Dennis et al discloses using a GGGS (SEQ ID NO: 5) linker. Dennis further discloses same in "Albumin binding as a general strategy for improving the pharmacokinetics of proteins", J Biol Chem. 2002 Sep. 20; 277(38):35035-43. doi: 10.1074/jbc.M205854200. Epub 2002 Jul. 15 where Dennis wrote that the dissociation equilibrium constant of peptide SA21 was determined to be 266 (rat), 320 (rabbit), and 467 (human) albumin with a half-life of 2.3 hours. Dennis further writes in the patent publication that, "In addition, it was discovered that the GGGS (SEQ ID NO: 5) linker sequence used between the Fab and the peptide could be deleted without significantly affecting albumin binding." (Paragraph [0210])

There is a need in the art to provide a peptide construct that binds active proteins to circulating albumin with a smaller dissociation constant and longer half-life than is presently achieved with the above referenced small peptide albumin binders.

SUMMARY OF THE DISCLOSED TECHNOLOGY

Novel albumin binding constructs enhance the pharmacokinetic performance of therapeutic peptides and proteins, lengthening half lives thereof in the body and reducing necessary administering of drugs to further spaced increments. Central to the novel constructs discovered is an amino acid sequence incorporating the core peptide DICLPRWGCLW (SEQ ID NO: 1), covalently linked to hydrophilic and flexible glycine-serine (Gly-Ser) linkers of the formula (ggs)xgg where X can be 3 to 8. These novel constructs comprising the core sequence and the (ggs)xgg linker, where the embodiment can be GGSGGSGGSGGR-LIEDICLPRWGCLWEDD (SEQ ID NO: 4), facilitate robust binding affinity to albumin, characterized by a binding dissociation constant of less than 20 nanomolar to human serum albumin. Some instances of the constructs may feature the core peptide SEQ 2, RLIEDICL-PRWGCLWEDD (SEQ ID NO: 2) as a foundational element, with GGSGGSGGSGG (SEQ ID NO: 3) linker strategically attached to one end, forming the preferred novel albumin construct GGSGGSGGSGGRLIEDICL-PRWGCLWEDD (SEQ ID NO: 4) ensuring both flexibility and hydrophilicity critical for effective albumin interaction. Some embodiments of these constructs may allow for the recombinant fusion and expression of active proteins, such as Klotho, at a terminal end comprising the preferred construct which can be then non-covalently associated with albumin. This binding strategy, in the some embodiments, preserves the biological activity of the protein while capitalizing on albumin's extended half-life in circulation.

Embodiments of the disclosed technology are assembled using cellular protein expression methodologies, including systems such as Chinese Hamster Ovary (CHO), Human Embryonic Kidney 293 (HEK293), and Transgenic Insect Cells, to ensure scalability and efficiency in production of the constructs. Upon administration into mammalian or avian subjects, the albumin binding constructs may exhibit a prolonged half-life comparable to at least 90% of the native albumin half-life in the respective species. Specific embodiments of the invention feature a alpha Klotho with the terminal GGSGGSGGSGGRLIEDICLPRWGCLWEDD (SEQ ID NO: 4) having a binding dissociation coefficient to FGF23 within the range of 15 to 30 nanomolar, with optimized constructs achieving a coefficient of 16.2 nanomolar which demonstrates that the binding ability of the novel construct for binding FGF23 is not diminished compared to the wild type Klotho. Importantly, using the preferred embodiments these constructs may be designed to minimize antigenicity when administered in vivo, ensuring compatibility and safety for therapeutic applications aimed at improving drug delivery efficacy and patient outcomes.

DETAILED DESCRIPTION OF EMBODIMENTS OF THE DISCLOSED TECHNOLOGY

An albumin binding construct comprises an amino acid sequence centered around the core peptide DICL-PRWGCLW (SEQ ID NO: 1). This core peptide is attached to at least one natural glycine-serine (Gly-Ser) amino acid sequence with the formula (ggs)xgg where x is from 3 to 8 and the constructs show hydrophilicity and flexibility. The inclusion of the GGSGGSGGSGG (SEQ ID NO: 3) sequence in the novel albumin binding construct not only enhances the flexibility of the construct but also significantly improves its binding affinity to albumin. This enhanced albumin binding affinity is quantified by an unprecedentedly low binding dissociation constant (Kd) value of less than 20 nanomolar with human albumin in some of the recombinantly expressed constructs, indicating a strong and stable interaction with albumin, thus ensuring that the therapeutic peptides and proteins maintain extended half-lives in the circulatory system, thereby enhancing therapeutic efficacy.

Naturally occurring glycine-serine amino acid chains or linkers of the formula (ggs)xgg are highly hydrophilic and flexible within three-dimensional space and, thus enabling proteins, enzymes, substrates, and other biochemical compounds to assume various orientations. When this specific series of glycine serine linker (ggs)xgg is combined with the core peptide to produce the novel albumin binding construct GGSGGSGGSGGRLIEDICLPRWGCLWEDD (SEQ ID NO: 4), unexpected characteristics allow for an unprecedented very low binding dissociation constants (less than 20 nanomolar) with human albumin as well as several other large mammalian species such as canines. For purposes of this disclosure, a biomolecule is said to be "naturally occurring" if said biomolecule is found in living organisms without artificial intervention or insertion.

A Glycine-Serine (Gly-Ser) linker is a sequence of amino acids comprised of repeating units of glycine and serine amino acids. Glycine, being the smallest amino acid with a hydrogen as its side chain, provides minimal steric hindrance and high flexibility, while serine, with a hydroxyl group, contributes to the linker's hydrophilicity, allowing for effective interaction with aqueous environments.

Albumin is a main protein of blood plasma, maintaining the oncotic pressure necessary for proper distribution of body fluids between body tissues and the bloodstream. It also serves as a carrier protein for various substances, including hormones, vitamins, and drugs. The binding constructs thus target albumin for binding, as it can circulate active proteins bound thereto to organs, tissues, and cells throughout the body. A biomolecule is said to be "active" if it is in a conformation with which it can perform its typical function. Thus, a denatured protein is not said to be active.

The binding dissociation constant (Kd) is a measure of the affinity between two binding partners, such as a peptide and albumin. A lower Kd value indicates a higher affinity, meaning the peptide binds more tightly to albumin. In this context, a Kd of less than 20 nanomolar (nM) indicates strong binding.

Albumin binding constructs in embodiments of the disclosed technology comprise a core peptide DICLPRWGCLW (SEQ ID NO: 1), which comprises 11 amino acids in sequence: Aspartic acid (D), Isoleucine (I), Cysteine (C), Leucine (L), Proline (P), Arginine (R), Tryptophan (W), Glycine (G), Cysteine (C), Leucine (L), and Tryptophan (W). The core peptide, in some embodiments, is part of a larger SA21 RLIEDICLPRWGCLWEDD (SEQ ID NO: 2) peptide, comprising a distal end connected to an 11-glycine-serine preferred linker resulting in the novel albumin binding construct GGSGGSGGSGGRLIEDICLPRWGCLWEDD (SEQ ID NO: 4) This structure when combined by recombinant expression with a natural alpha Klotho shows significant binding to canine albumin at approximately 8 nanomolar and also binds to FGF-23 at a rate similar to wild-type counterparts. Using this peptide, binding efficiency is improved, thereby lengthening the half lives of active proteins bound thereto.

The disclosed technology, in some embodiments, is used with other proteins, such as follistatin used in anti-obesity treatments or treatments for sarcopenia. Active proteins bound to the novel albumin binding construct GGSGGSGGSGGRLIEDICLPRWGCLWEDD (SEQ ID NO: 4) have a half life in the human body of approximately 19 days, as opposed to current pharmaceuticals where constructs using fatty acid binders for albumin binding typically have half lives of from 4 to 7 days in the body. Thus the novel therapeutics using the novel albumin binder might be effectively dosed monthly as opposed to current weekly regimes with fatty acid binders.

In carrying out an embodiment of the disclosed technology, the core peptide was bound to glycine-serine rich amino acid sequences by encoding the recombinant expression resulting in the albumin binding construct GGSGGSGGSGGRLIEDICLPRWGCLWEDD (SEQ ID NO: 4) being attached to the terminal end of the alpha Klotho molecule under recombinant expression. The resultant kD of this novel Klotho was recorded to be less than 19 nM when measured against canine albumins. The disclosed technology is, in embodiments, used to improve the kD values of various peptides with respect to albumin binding, where the natural peptides have a long half life, can be modified with natural amino acids, or truncated; thus the peptides are protected from degradation. Following this, the peptides can be expressed as a recombinant protein with GGSGGSGGSGGRLIEDICLPRWGCLWEDD (SEQ ID NO: 4) with the desired therapeutic peptide at one of the terminal ends. This results in a follistatin with a 7 day half life in canine. Cost of production is also reduced in using a transgenic insect cell that can fold and glycosylate 3 dimensional eukaryotic proteins and express the albumin binder with the required cysteine cyclization The constructs are effective across various mammalian species, including rats, rabbits, horses, felines, canines, and humans.

The constructs are typically produced by cellular protein expression, wherein a plasmid DNA fragment coding for the components of the construct are transfected into the genome of a target cell. Such target cells may be Chinese Hamster Ovary (CHO) cells, Human Embryonic Kidney 293 (HEK293) cells, and Transgenic Insect Cells.

The albumin binding constructs are expressed as part of the recombinant expression of the active three-dimensional proteins, such as mammalian Klotho (National Library of Medicine, Indices NM_004795 and NM_013823) without compromising the activity of the three-dimensional protein or its binding activities to substrates. The disclosed technology is significantly less antigenic than albumin-binding peptide or antibody technologies disclosed in prior art, thereby increasing safety for clinical use and mitigating concern of immunogenic response due to large, globular, and foreign entrants into the circulatory system.

The linker used in embodiments of the disclosed technology is GGSGGSGGSGG (SEQ ID NO: 3), which is a hydrophilic and flexible linker. This linker forms a spiral spring which binds to the SA21. Within a 30 amino acid sequence, the linker binds to the albumin. In other embodiments the linker is GGSGGSGGSGG (SEQ ID NO: 3) used in an 11d-amino acids glycine/serine series. A full sequence (linker and amino acid) in some embodiments is GGSGGSGGSGGRLIEDICLPRWGCLWEDD (SEQ ID NO: 4).

We can cite Dennis who says in paragraph 210 that the GGGS (SEQ ID NO: 5) binder they used had no effect upon the binding constants of their constructs wherever partially or totally removed so that anyone would assume that a glycine/serine linker attached to the above core would have no effect upon its albumin binding abilities Binding of klotho to FGF23, as carried out in embodiments of the disclosed technology, forms a complex that binds to fibroblast growth factor receptor.

The interaction between native human albumin protein and mouse klotho protein was determined by way of using embodiments of the disclosed technology, as follows. The tests were carried out by KMD Bioscience CO., Ltd.

TABLE 1

Sample information

| Name | MW · (Da) | Concentration | Buffer |
|---|---|---|---|
| Human Albumin | 74000 | 20 mg/mL | / |
| Mouse klotho | 108000 | 0.4 mg/mL | PBS, 0.5M Arginine, 5 mM GSH, 1 mM GSSG, pH 7.4 |

TABLE 2

Experimental instruments and parameters

| Name | Details |
|---|---|
| OpenSPR TM | Nicoya |
| Sensor Chip COOH | SHF1101 |
| (SEN-AU-100-10-HC-COOH) | (Nicoya) |
| TraceDrawer | Ridgeview, Instrumentab, Sweden |

TABLE 3

Reagent Information

| Name | Vendor | Cat. No. | Lot No. |
|---|---|---|---|
| HEPES | Sigma-Aldrich | H3375-250G | 1003380610 |
| EDTA | SCR | 10009717 | 20180122 |
| NaCl | SCR | 10019318 | 20211115 |
| Tween 20 | Beyotime | ST825-500 ml | NA |
| BSA | Solarbio | A8020 | 1010F051 |
| Glycine 1.5 | Cytiva | BR100354 | NA |
| EDC | Sigma-Aldrich | E1769-25G | 102421111 |
| NHS | Sigma-Aldrich | 130672-25G | WXBD6833V |
| Ethanolamine hydrochloride | Sigma-Aldrich | E6133-100G | SHBF6036V |

TABLE 4

Buffer information

| Name | Details |
|---|---|
| Activation buffer | 400 mM EDC + 100 mM NHS |
| Blocking buffer | 1M Ethanolamine hydrochloride |
| Immobilization Buffer | 10 mM Sodium Acetate, pH 4.0 |

TABLE 4-continued

Buffer information

| Name | Details |
|---|---|
| Ligand Buffer | HEPES(pH 7.4): 10 mM HEPES, 150 mM NaCl, 3 mM EDTA, 0.005% Tween 20. |
| Analyte Buffer | HEPES(pH 7.4): 10 mM HEPES, 150 mM NaCl, 3 mM EDTA, 0.005% Tween 20. |
| Regeneration Buffer | 10 mM Glycine-HCl, pH 1.5 |

The activator was prepared by mixing 400 mM EDC and 100 mM NHS immediately prior to injection. The (sensor) chip was activated for 240 seconds with the mixture at a flow rate of 20 uL/min. Native human Albumin Protein was diluted to 10 μg/mL in an immobilization buffer, then injected to sample channel at a flow rate of 20 uL/min. The chip is deactivated by 1 M Ethanolamine hydrochloride at a flow rate of 20 uL/min for 240 s. The Chip is a low capacity two-dimensional surface chemistry that comprises a polyethylene glycol (PEG) spacer terminated with carboxylic acids. This surface is particularly useful where lectin binding may occur or where carboxymethyl dextran (CMD) coatings are not desired.

Mouse klotho protein was diluted with the analyte buffer to 6 concentrations (40, 20, 10, 5, 2.5 and 0 nM). Mouse klotho protein was then injected to sample channel at a flow rate of 20 uL/min for an association phase of 240 s, followed by 360 s dissociation. The association and dissociation process were carried out with the analyte buffer. Six cycles of analyte were tested using the analyte concentrations listed above, in ascending order. After each cycle of interaction analysis, the sensor chip surface should be regenerated completely with 10 mM Glycine-HCl as injection buffer at a flow rate of 150 uL/min for 10 s to remove the analyte, then next concentration cycle of the Analyte mouse klotho protein need to repeat injection and Regeneration steps.

The results of the tests were as follows:

Kinetic Affinity: Native Human Albumin Protein & Mouse Klotho Protein

TABLE 5

Kinetic and affinity parameters

| Parameter | Paraphrase | ResuLt |
|---|---|---|
| ka (1/(M*s)) | Association rate constant | 8.58E5 |
| kd (1/s) | Dissociation rate constant | 6.81E-3 |
| KD (M) | The dissociation equilibrium constant, also called the affinity constant | 7.94E-9 |

Native human Albumin Protein immobilized on COOH chip can bind Mouse klotho Protein with an affinity constant of 7.94 nM as determined in a SPR assay.

Any device or step to a method described in this disclosure can comprise or consist of that which it is a part of, or the parts which make up the device or step. The term "and/or" is inclusive of the items which it joins linguistically and each item by itself. "Substantially" is defined as at least 95% of the term being described and/or "within a tolerance level known in the art and/or within 5% thereof. Any device or aspect of a device or method described herein can be read as "comprising" or "consisting" thereof.

SEQUENCE LISTING

```
Sequence total quantity: 5
SEQ ID NO: 1              moltype = AA   length = 11
FEATURE                   Location/Qualifiers
source                    1..11
                          mol_type = protein
                          organism = synthetic construct
SEQUENCE: 1
DICLPRWGCL W                                                                11

SEQ ID NO: 2              moltype = AA   length = 18
FEATURE                   Location/Qualifiers
source                    1..18
                          mol_type = protein
                          organism = synthetic construct
SEQUENCE: 2
RLIEDICLPR WGCLWEDD                                                         18

SEQ ID NO: 3              moltype = AA   length = 11
FEATURE                   Location/Qualifiers
source                    1..11
                          mol_type = protein
                          organism = synthetic construct
SEQUENCE: 3
GGSGGSGGSG G                                                                11

SEQ ID NO: 4              moltype = AA   length = 29
FEATURE                   Location/Qualifiers
source                    1..29
                          mol_type = protein
                          organism = synthetic construct
SEQUENCE: 4
GGSGGSGGSG GRLIEDICLP RWGCLWEDD                                             29

SEQ ID NO: 5              moltype = AA   length = 4
FEATURE                   Location/Qualifiers
source                    1..4
                          mol_type = protein
                          organism = synthetic construct
SEQUENCE: 5
GGGS                                                                         4
```

I claim:

1. An albumin binding construct, comprising: an SA21 peptide comprising a core peptide DICLPRWGCLW (SEQ ID NO: 1) covalently attached to a c-terminus of a glycine-serine linker comprising a sequence of GGSGGSGGSGG (SEQ ID NO: 3);

said glycine-serine linker being hydrophilic and flexible, wherein the albumin binding constructs binds to human albumin with a binding dissociation constant value of less than 20 nanomolar to human albumin.

2. The albumin binding construct of claim 1, wherein said albumin binding construct is produced recombinantly.

3. The albumin binding construct of claim 2, wherein said albumin binding construct is produced in at least one of the following cell systems: Chinese Hamster Ovary, Human a Embryonic Kidney 293, or a Transgenic Insect Cell.

4. The albumin binding construct of claim 1, further comprising an alpha Klotho and the binding dissociation coefficient of said Klotho to FGF23 is in the range of 15 nanomolar to 30 nanomolar as is the same as natural klotho binding to FGF23.

5. The albumin binding construct of claim 4, wherein said binding dissociation coefficient of Klotho to FGF23 is 16.2 nanomolar.

* * * * *